US006663663B2

United States Patent
Kim et al.

(10) Patent No.: US 6,663,663 B2
(45) Date of Patent: Dec. 16, 2003

(54) STENT

(75) Inventors: Cheol-Sang Kim, Jeonju (KR); Sung-Soon An, Seoul (KR); Chull-Su Lim, Seoul (KR)

(73) Assignee: M.I. Tech Co., Ltd., Pyungtaek (KR)

(*) Notice: Subject to any disclaimer, the term of this patent is extended or adjusted under 35 U.S.C. 154(b) by 0 days.

(21) Appl. No.: 09/855,732

(22) Filed: May 14, 2001

(65) Prior Publication Data
US 2002/0169498 A1 Nov. 14, 2002

(51) Int. Cl.[7] .................................................. A61F 2/06
(52) U.S. Cl. ...................... 623/1.15; 623/1.13; 623/1.14; 623/1.16
(58) Field of Search ................................ 623/1.13–1.16

(56) References Cited

U.S. PATENT DOCUMENTS

| | | | | |
|---|---|---|---|---|
| 5,330,500 A | * | 7/1994 | Song | 606/198 |
| 5,575,818 A | * | 11/1996 | Pinchuk | 623/1.15 |
| 5,800,456 A | * | 9/1998 | Maeda et al. | 606/198 |
| 5,843,167 A | * | 12/1998 | Dwyer et al. | 623/1.16 |
| 5,897,589 A | * | 4/1999 | Cottenceau et al. | 623/1.16 |
| 6,066,169 A | * | 5/2000 | McGuinness | 623/1.16 |
| 6,113,612 A | * | 9/2000 | Swanson et al. | 606/153 |
| 6,146,416 A | * | 11/2000 | Andersen et al. | 623/1.15 |
| 6,187,036 B1 | * | 2/2001 | Shaolian et al. | 623/1.15 |
| 6,224,627 B1 | * | 5/2001 | Armstrong et al. | 623/1.23 |
| 6,241,757 B1 | * | 6/2001 | An et al. | 623/1.1 |

FOREIGN PATENT DOCUMENTS

| WO | WO 99/29262 | * | 6/1999 | A61F/2/06 |
|---|---|---|---|---|

OTHER PUBLICATIONS

Pub. No.: US 2002/0032481 A1 Gabbay.*

* cited by examiner

Primary Examiner—David H. Willse
Assistant Examiner—Javier G. Blanco
(74) Attorney, Agent, or Firm—Christie, Parker & Hale, LLP

(57) ABSTRACT

A stent includes a first turn made of a wire having a unit length. The first turn is formed having a plurality of first straight sections connected to each other by a plurality of bending points along a circumferential plane and a plurality of valleys and peaks formed by the bending points. The stent further includes a first intersection turn made of a wire having a unit length, the first intersection turn is formed having a plurality of straight sections intersecting the first straight sections to form a plurality of meshes, the straight sections of the intersection turn formed by a plurality of peaks and valleys.

7 Claims, 4 Drawing Sheets

STENT

BACKGROUND OF THE INVENTION (a) Field of the Invention

The present invention relates to a stent, and more particularly, to a stent which can be easily pushed out of an introducer when it is introduced into an internal wall by a pusher.

(b) Description of the Related Art

Generally, a stent is introduced into a stricture portion of an internal wall such as a blood vessel, a bilious track, and an esophagus to enlarge the stricture portion of the internal wall and maintain the enlarged stricture portion.

Such a stent is cylindrical and self-expandable so that it can be contracted by outer force. The self-expandable stent is classified into a spiral type and a zig-zag type.

The zig-zag type stent comprises a plurality of turns made of a wire having a unit length. Each of the turns comprises a plurality of straight sections joined one another by a plurality of bending points such that it has a plurality of valleys and peaks. The valleys of a turn are interlocked with peaks of an adjacent turn.

To dispose the stent on the stricture portion of the internal wait, the stent is first contracted in the smaller diameter and inserted in an introducer. In this state, the introducer is inserted into the internal wall and the stent is pushed out of the introducer by a pusher so that it is located on the internal wall, while being extended lengthwise.

However, since the turns are connected to each other at the valleys and peaks, the sufficient pushing force cannot be obtained when the stent is pushed by the pusher. In addition, a size of each mesh formed by the connection of the valleys and peaks is so large, the flexibility of the stent is deteriorated, and the cancer can be easily penetrated into the stent through the mesh.

Furthermore, since the conventional stent is simply formed in the cylindrical shape, it may be displaced from the desired location to other portion.

SUMMARY OF THE INVENTION

Therefore, the present invention has been made in an effort to solve the above problems.

It is an objective of the present invention to provide a stent which can be easily pushed out of an introducer when it is located in an internal wall.

It is another objective of the present invention to provide a stent that can be designed such that a size of meshes can be minimized, while increasing the number of meshes.

It is still another objective of the present invention to provide a stent that can be prevented from being moved in a state where it is disposed in the internal wall.

To achieve the above objectives, the present invention provides a stent comprising a first turn made of a wire having a unit length, the first turn being formed having a plurality of first straight sections connected to each other by a plurality of bending points along a circumferential plane and a plurality of valleys and peaks formed by the bending points; and a first intersection turn made of a wire having a unit length, the first intersection turn being formed having a plurality of straight sections intersecting the first straight sections to form a plurality of meshes, the straight sections of the intersection turn formed by a plurality of peaks and valleys.

The stent may further comprise a second turn and a second intersection turn, the valleys of the first turn being interlocked with peaks of the second turn, the valleys of the first intersection turn being interlocked with the peaks of the second intersection turn.

One of the straight sections of the first intersection turn is twisted on one of the straight sections of the first turn at least more than one time.

One of the straight sections of the first intersection turn is twisted on intersection points of the straight sections of the first turn and the first intersection turn.

The first turn and the first intersection turn are formed in an identical cycle. The first turn and the first intersection turn are formed having an identical width to each other.

One of the first turn and the first intersection turn comprises an anti-migration turn for preventing the stent from being moved out of a desired portion of an internal wall.

The anti-migration turn comprises a flare turn formed on one end of one of the first turn and the first intersection turn, a diameter of the fare turn being increasingly increased from the one end.

BRIEF DESCRIPTION OF THE DRAWINGS

The accompanying drawings, which are incorporated in and constitute a part of the specification, illustrate an embodiment of the invention, and, together with the description, serve to explain the principles of the invention.

DETAILED DESCRIPTION OF THE PREFERRED EMBODIMENTS

Preferred embodiments of the present invention will be described hereinafter with reference to the accompanying drawings.

Figure 1:
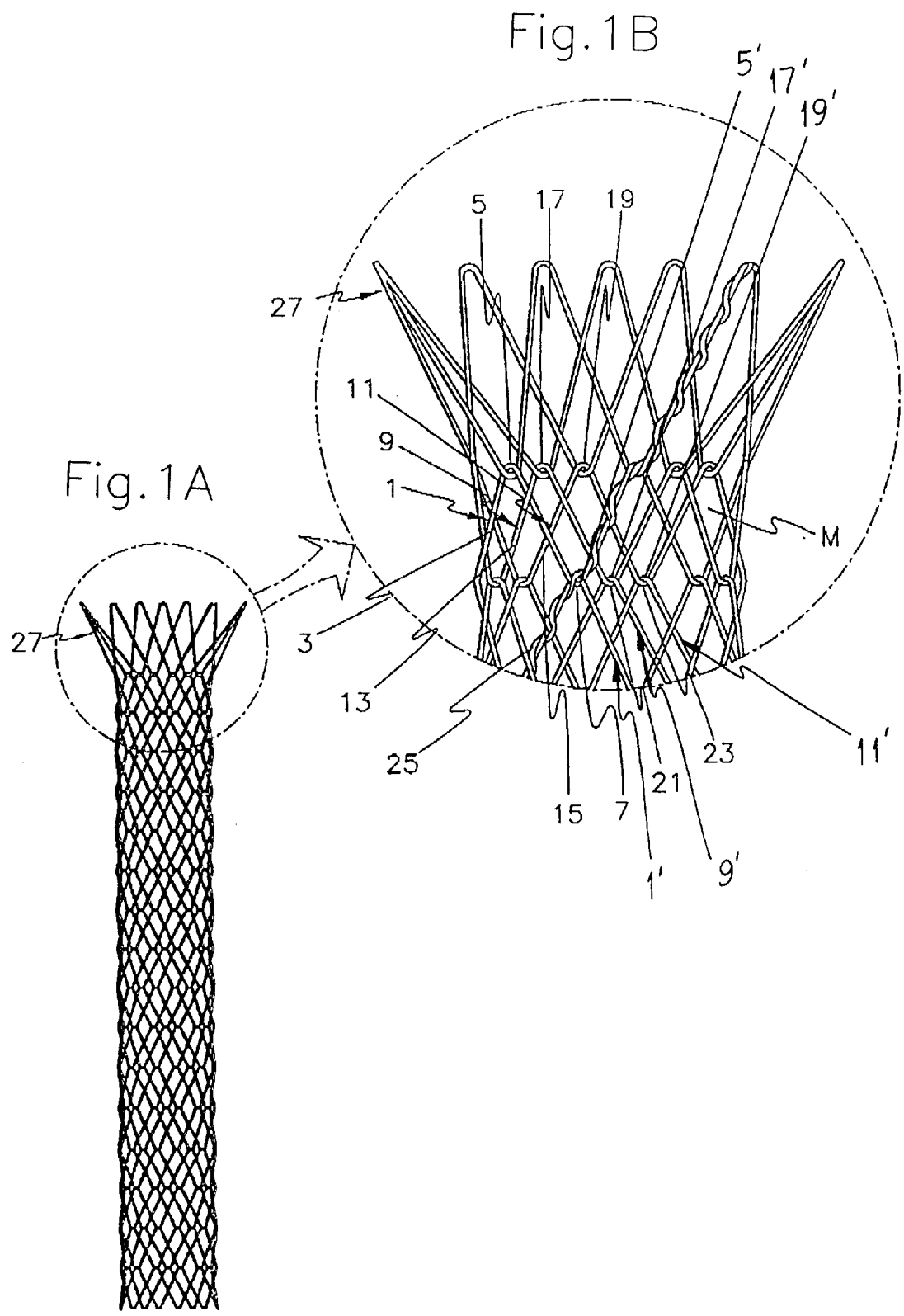
FIG. 1*a* is a perspective view of a stent according to a first embodiment of the present invention.
FIG. 1*b* is a close-up perspective view of a stent according to a first embodiment of the present invention.
Figure 2:
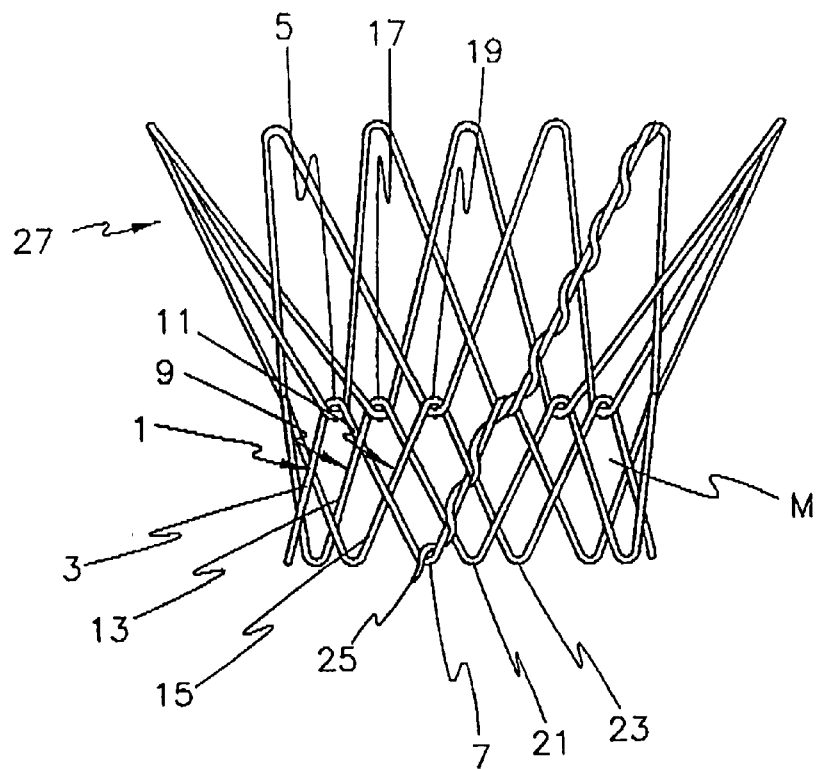
FIG. 2 is a side view illustrating a connection state of a first turn and intersection turns of a stent according to a first embodiment of the present invention.
Figure 3:
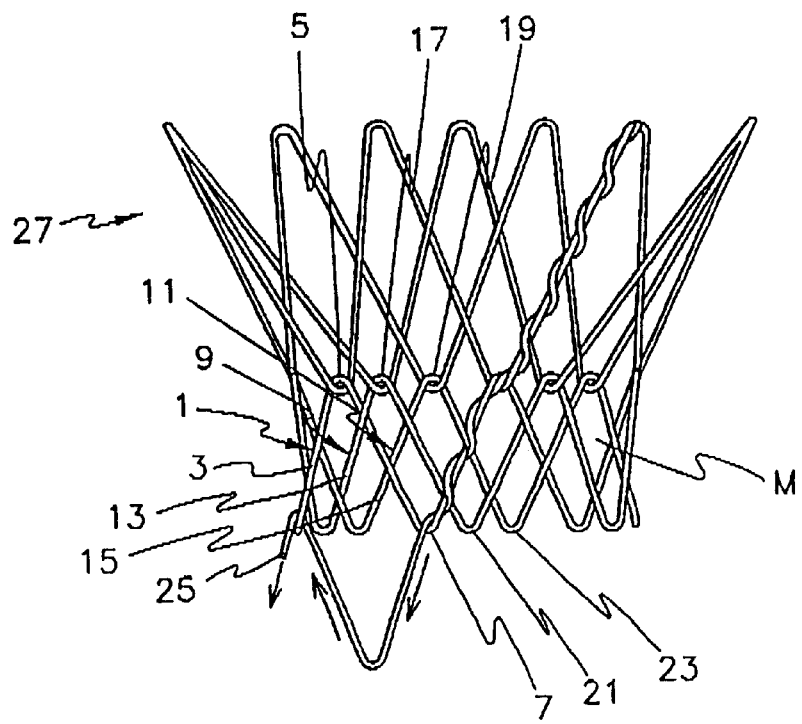
FIG. 3 is a side view illustrating a connection state of connecting portions of a stent according to a first embodiment of the present invention.

FIGS. 1 to 3 show a stent according to a first preferred embodiment of the present invention.

The inventive stent is made of a wire having a predetermined length. To make a stent in a cylindrical shape using the wire, a first turn 1 is formed having a plurality of first straight sections 3 connected to each other by a plurality of bending points along a circumferential plane and a plurality of valleys and peaks 5 and 7 formed by the bending points.

After the first turn 1 is formed, as shown in FIG. 2, first and second intersection turns 9 and 11 are formed on the circumferential plane along which the first turn 1 is formed. The first intersection turn 9 comprises a plurality of straight sections 13 connected to each other by a plurality of bending points forming valleys and peaks 21 and 17 and disposed at a predetermined phase difference from the straight sections 3 of the first turn 1 such that the straight sections 13 of the first intersection turn 9 intersect the straight sections 3 of the first turn 1. The second intersection turn 11 also comprises a plurality of straight sections 15 connected to each other by a plurality of bending points forming valleys and peaks 23 and 19 and disposed at a predetermined phase difference from the straight sections 3 and 13 of the respective first turn and first intersection 1 and 9. By the intersection between the first turn 1 and the first and second intersection turns 9 and 11, meshes M are formed on the stent.

The first turn 1 and the first and second intersection turns 9 and 11 are formed with an identical cycle or a different cycle.

In addition, widths of the first turn 1 and the first and second intersection turns 9 and 11 may be identical or not. The peaks 5, 17 and 19 and valleys 7, 21 and 23 of the first turn 1 and the intersection turns 9 and 11 are formed at a predetermined distance from each other. The straight sections 3, 13 and 15 are symmetrically formed on the basis of the peaks and valleys and have an identical length.

The valleys 7 of the first turn 1 are interlocked with peaks 5' of an adjacent first turn 1'. The valleys 21 and 23 of the intersection turns 9 and 11 are interlocked with peaks 17' and 19' of adjacent intersection turns 9' and 11'.

One end portions of the intersection turns 9 and 11 are twisted on the straight section of the first turn 1 so that they can securely connected with the first turn 1.

The end portions 25 are formed by being twisted more than one time on the intersection point of the first turn 1 and the first and second intersection turns 9 and 11 so that the stent can be extended lengthwise when it is expanded from a contract state.

It is more preferable that the wire is made of a shape memory alloy such as Nitinol so that the stent can be efficiently expanded in the radial direction.

By connection of the valleys 7, 21 and 23 with the adjacent peaks 5', 17', and 19', a mesh structure M is formed.

Front or rear ends of the wire may be interconnected with or twisted on the straight section of the first turn 1.

In addition, the inventive stent is further provided with an anti-migration portion 27 that can prevent the stent disposed on the stricture portion of the internal wall from being moved to other portion.

The anti-migration portion 27 is formed by enlarging the diameter of at least one end of the first turn 1 and the intersection turns 9 and 11 such that the one end is outwardly inclined in the radial direction at a predetermined angle so that the first turn 1 or the intersection turns 9 and 11 are inserted into the internal wall when the stent is disposed on the stricture portion.

The anti-migration portion 27 is integrally formed with the first turn 1 or the intersection turns 9 and 11 with an identical central axis so that it can be easily expanded and contracted when it is disposed on the internal wall.

Figure 4:
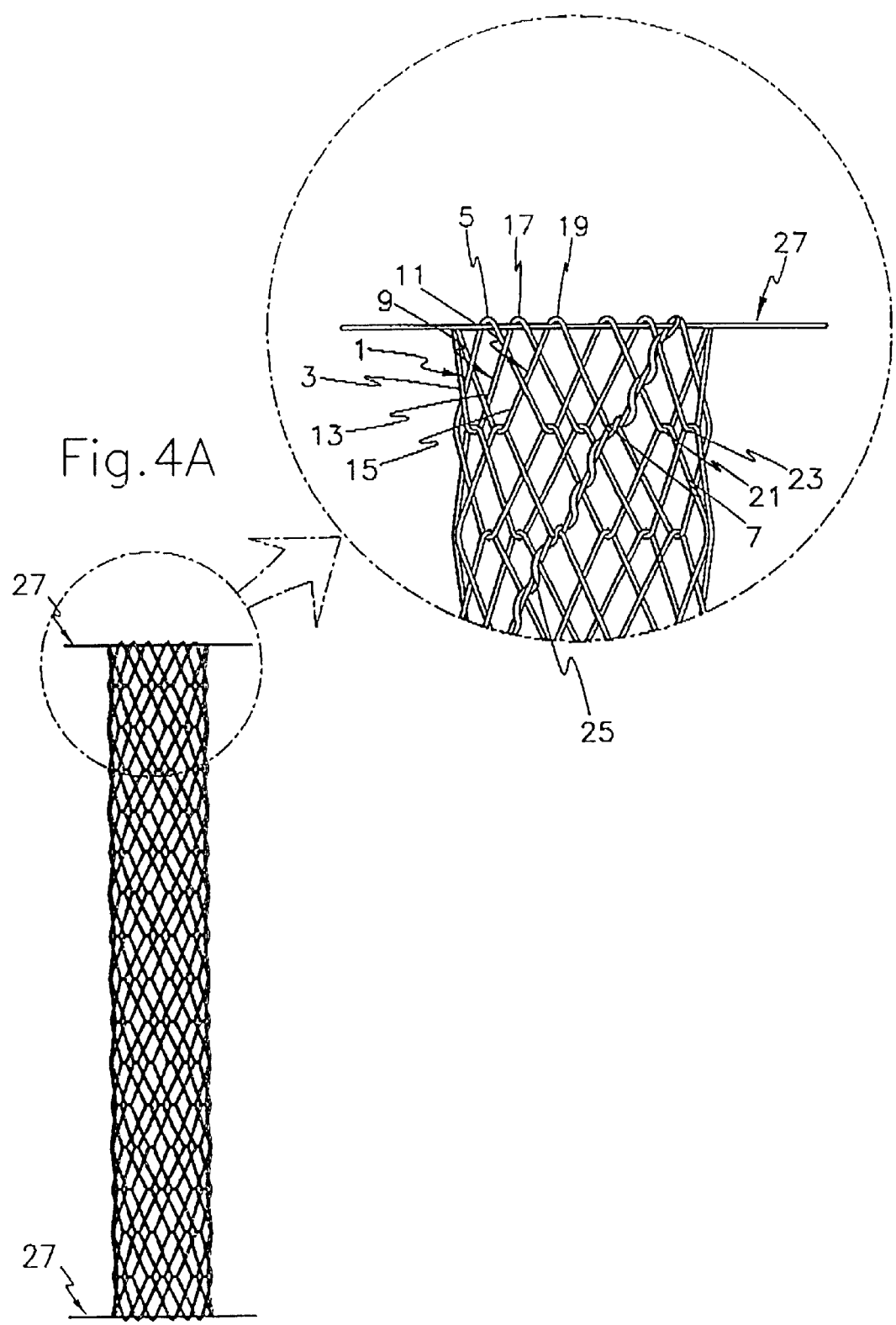
FIG. 4*a* is a side view of a stent according to a first embodiment of the present invention.
FIG. 4*b* is a close-up side view of a stent according to a second embodiment of the present invention.
Figure 5:
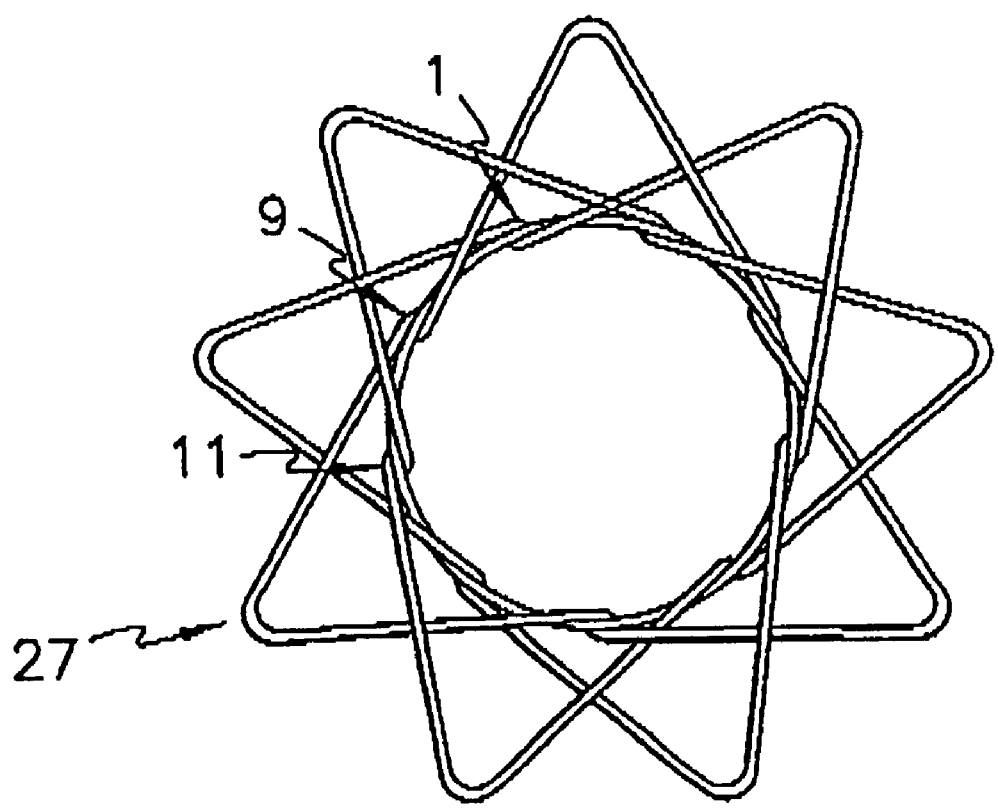
FIG. 5 is a plane view of a stent according to a second embodiment of the present invention.

The anti-migration portion 27 is formed in a flare type. That is, as shown in FIGS. 1a and 1b, a diameter of one end portion of the first turn 1 or the intersection turns 9 and 11 is enlarged. As another embodiment, as shown in FIGS. 4a and 4b, the anti-migration portion can be formed to be protruded in a perpendicular direction with respect to the central axis.

In addition, the first turn 1, the intersection turns 9 and 11, and the connecting portion 25, and the anti-migration portion 27 may be covered with a covering member (not shown) such as polymer.

As described above, since the straight sections 13 and 15 of the intersection turns 9 and 11 are disposed to intersect the straight sections 3 of the first turn 1, the number of meshes M of the stent is increased and the size of each mesh M is reduced.

In addition, as shown in FIG. 3, by the connecting portion 25, the straight sections 3, 13 and 15 are connected by the twist, the extending force in the lengthwise direction when the stent is expanded from the contract state is enhanced.

In addition, since the meshes are densely formed by the intersection turns 9 and 11, the infiltration of an organization cell such as cancer can be prevented.

Furthermore, since the anti-migration portion 27 is embedded in the internal wall, the displacement of the stent in the internal wall can be prevented.

While this invention has been described in connection with what is presently considered to be the most practical and preferred embodiment, it is to be understood that the invention is not limited to the disclosed embodiments, but, on the contrary, is intended to cover various modifications and equivalent arrangements included within the spirit and scope of the appended claims.

What is claimed is:

1. A stent comprising:
   a first turn formed by a wire having a predetermined length, the wire being bent in a zig-zag shape having plural first straight sections interconnected by plural valleys and peaks to define a cylindrical shape;
   an adjacent first turn formed in a zig-zag shape having plural second straight sections interconnected by plural peaks and valleys, wherein the peaks are interlocked with the corresponding valleys of the first turn;
   a first intersection turn formed in a zig-zag shape having plural third straight sections interconnected by plural valleys and peaks to define a cylindrical shape, the third straight sections intersecting the corresponding first straight sections of the first turn; and
   an adjacent first intersection turn formed in a zig-zag shape having plural fourth straight sections interconnected by plural peaks and valleys, wherein the peaks are interlocked with the corresponding valleys of the first intersection turn the fourth straight sections intersecting the corresponding second straight sections of the adjacent first turn.

2. The stent of claim 1, further comprising a second intersection turn formed in a zig-zag shape having plural fifth straight sections interconnected by plural peaks and valleys, the fifth straight sections intersecting the corresponding first and second straight sections.

3. The stent of claim 1 wherein one of the straight sections of the first intersection turn is twisted on one of the straight sections of the first turn at least more than one time.

4. The stent of claim 1 wherein one of the straight sections of the first intersection turn is twisted on intersection points of the straight section of the first turn and the first intersection turn.

5. The stent of claim 1 wherein the first turn and the first intersection turn are formed in an identical cycle.

6. The stent of claim 1 wherein the first turn and the first intersection turn are formed having an identical width to each other.

7. The stent of claim 1 wherein one of the first turn and the first intersection turn comprises an anti-migration turn for preventing the stent from being moved out of a desired portion of an internal wall.

\* \* \* \* \*